(12) United States Patent
Mycek et al.

(10) Patent No.: US 8,068,898 B2
(45) Date of Patent: Nov. 29, 2011

(54) FLUORESCENCE LIFETIME SPECTROMETER (FLS) AND METHODS OF DETECTING DISEASED TISSUES

(75) Inventors: Mary-Ann Mycek, Ann Arbor, MI (US);
Ethan Dmitrovsky, Hanover, NH (US);
Jonathan Pitts, Westford, MA (US)

(73) Assignee: Trustees of Dartmouth College, Hanover, NH (US)

( * ) Notice: Subject to any disclaimer, the term of this patent is extended or adjusted under 35 U.S.C. 154(b) by 430 days.

(21) Appl. No.: 10/469,021

(22) PCT Filed: Feb. 28, 2002

(86) PCT No.: PCT/US02/05980
§ 371 (c)(1),
(2), (4) Date: Aug. 26, 2003

(87) PCT Pub. No.: WO02/069784
PCT Pub. Date: Sep. 12, 2002

(65) Prior Publication Data
US 2004/0073119 A1  Apr. 15, 2004

(51) Int. Cl.
*A61B 6/00* (2006.01)

(52) U.S. Cl. .......................... 600/478; 600/476
(58) Field of Classification Search .......... 600/309–344, 600/473–480, 407, 408
See application file for complete search history.

(56) References Cited

U.S. PATENT DOCUMENTS

| | | | | |
|---|---|---|---|---|
| 5,369,496 A * | 11/1994 | Alfano et al. | ................. | 356/446 |
| 5,713,364 A * | 2/1998 | DeBaryshe et al. | .......... | 600/476 |
| 5,772,588 A * | 6/1998 | Miwa et al. | ................... | 600/310 |
| 5,813,987 A * | 9/1998 | Modell et al. | ................ | 600/473 |
| 6,070,093 A * | 5/2000 | Oosta et al. | ................... | 600/316 |
| 6,201,989 B1 | 3/2001 | Whitehead et al. | ........... | 600/476 |
| 6,280,386 B1 | 8/2001 | Alfano et al. | ................. | 600/431 |
| 6,571,118 B1 * | 5/2003 | Utzinger et al. | ............. | 600/476 |
| 2004/0010192 A1 * | 1/2004 | Benaron et al. | ............... | 600/431 |

OTHER PUBLICATIONS www.tpub.com/neets/tm/111-4.htm.*

* cited by examiner

*Primary Examiner* — Sanjay Cattungal
(74) *Attorney, Agent, or Firm* — Licata & Tyrrell, P.C.

(57) ABSTRACT

This invention relates to method and apparatus for collection of the complete fluorescence emission spectrum and the transient decay of a selected spectral band simultaneously with data acquisition times of less that one second. This invention is useful for studying human tissues and cells in vivo.

1 Claim, 4 Drawing Sheets

FLUORESCENCE LIFETIME SPECTROMETER (FLS) AND METHODS OF DETECTING DISEASED TISSUES

Work on this invention was supported in part by a grant from the National Science Foundation (Grant No. BES-9977982) and the U.S. Government may have certain rights in this invention.

FIELD OF THE INVENTION

This invention relates to methods and apparatus for collection of the complete fluorescence emission spectrum and the transient decay of a selected spectral band simultaneously with data acquisition times of less than one second.

BACKGROUND OF THE INVENTION

Laser-induced fluorescence spectroscopy has been employed to probe complex biological systems, like cells and tissues, for biochemical and morphological alterations associated with early evidence of diseases, potentially leading to non-invasive diagnosis in vivo. Once diagnosed, such tissue may be treated at their earliest stages, reducing or preventing the risk of developing clinically apparent diseases that often have associated morbidity or mortality, like cancer.

Steady-state fluorescence spectroscopy has been explored as a non-invasive means of detecting both cancers and pre-neoplasia (pre-malignancy) in vivo. In tissue fluorescence spectroscopy, light is used to probe endogenous biological fluorophores like collagen, elastin, NADPH, and tryptophan. Because tissue is an inhomogeneous medium, fluorescence signals measured in vivo reflect tissue morphology and optical absorption and scattering properties, as well as local biochemistry. These signals provide detailed information regarding tissue microenvironment and disease in a non-invasive way. Because fluorescence spectroscopy can be performed with fiber optic probes, the technique is compatible with minimally invasive methods, thus allowing optical detection in internal regions of the body accessible with endoscopes or catheters. U.S. Pat. No. 6,062,591 discloses an arrangement and method for diagnosis of malignant tissue by fluorescent observation using a stroboscope as a white light source to illuminate tissues through an endoscope, while a laser stimulates the fluorescence. U.S. Pat. No. 5,377,676 discloses a method for determining the biodistribution of substances using fluorescence spectroscopy. U.S. Pat. No. 5,208,651 discloses an apparatus and method for measuring fluorescence intensities at a plurality of wavelengths.

However, while the spectrally resolved fluorescence measurements described above are relatively simple to implement clinically and appear to provide useful diagnostic information, there are certain limitations intrinsic to the steady-state spectral technique. Further, because spectrally resolved measurements are inherently intensity dependent, variations in intensity resulting from optical loss in the experimental system or optical absorption in complex media may affect the lineshape of the steady-state emission spectrum in unpredictable and unquantifiable ways. This is an important limitation to consider when applying fluorescence spectroscopy in vivo, since intensity losses attributed to hemoglobin absorption in tissue are routinely observed in vivo.

Limitations to spectrally resolved fluorescence measurements arise from the fact that these steady-state measurements integrate the emitted fluorescence signal over time, thus ignoring the dynamics of the fluorescence decay and losing an additional dimension of information. Time-resolved techniques capture the transient decay of the fluorescence intensity in time, which reflects the relative concentrations and the lifetimes of the endogenous fluorophores contributing to the emission. Because of band broadening due to molecular vibrations and non-radiant relaxation, the fluorescence emission spectrum of biomolecules is rather featureless and therefore may be relatively insensitive to local biochemical variations. Fluorophore lifetimes, which depend on both radiative and non-radiative decay mechanisms, are known to be extremely sensitive to the local biochemical environment and to vary with pH and oxygenation, both of which may differ between diseased and normal tissue. This was demonstrated explicitly for NADH, where the average lifetime was found to vary by a factor of approximately six between mitochondrial NADH and NADH in aqueous solution. Further, because fluorophore lifetime does not change with variations in excitation intensity or optical losses from hemoglobin absorption, time-resolved measurements are intensity independent.

Until recently, time-resolved fluorescence spectroscopy had been employed exclusively for in vitro diagnosis of tissue specimens, such as atherosclerotic plaque and malignant tumors. These early measurements used ultrashort laser pulses of picosecond duration for excitation and were therefore dependent upon large laser systems that would have been difficult to operate outside of the stable environment of a laser laboratory. Due to the relatively weak nature of fluorescence emission, detection was accomplished using highly sensitive photomultiplier tubes and time-correlated single-photon counting methods, which are time consuming and therefore require a static sample for measurement. For these reasons, technological limitations precluded the transfer of fluorescence lifetime spectroscopy from the laboratory to the clinic. The feasibility of using a time-resolved autofluorescence spectroscopy as a optical diagnostic technique for determining colonic polyp types in vivo, and the diagnostic accuracy of the technique was studied. (Mycek, M. A. et al., Gastrointestinal Endoscopy 1998, 48:4, 390-394)

The present invention relates to a portable Fluorescence Lifetime Spectrometer (FLS) designed to be compatible with both laboratory and clinical research studies on biological systems (cells and tissues), and which is useful to successfully discriminate cancerous and pre-cancerous tissues or cells from normal tissues or cells in vivo. The present invention also provides related methods for using the FLS to diagnose, pre-cancerous and cancerous tissues or cells and to distinguish from normal tissues or cells in vivo.

SUMMARY OF THE INVENTION

An object of the present invention is to provide an apparatus for measuring spectral and temporal fluorescence properties of tissue or cells simultaneously to detect precancerous and cancerous tissues in vivo.

Another object of the present invention is to provide a method for measuring spectral and temporal fluorescence properties of tissue or cells simultaneously in vivo.

Yet another object of the present invention is to provide a method for detecting precancerous and cancerous tissues or cells in vivo which comprises measuring spectral and temporal fluorescent properties of a tissue or cell sample in vivo simultaneously.

DETAILED DESCRIPTION OF THE INVENTION

In general, when light enters a complex, inhomogeneous medium such as biological tissue, a number of scattering, absorption, and emission events occur depending on the physical nature of the light and the specific morphology and composition of the tissue. Although complex, this optical response can be measured by a variety of spectroscopic techniques to obtain potential diagnostic information for the discrimination of diseased tissues from normal tissues.

The vast majority of fluorescence spectroscopy studies in tissues have resolved the spectral lineshape of the emission (the variation of fluorescence intensity with wavelength of emitted light) and examined differences between normal and diseased tissues. Because of molecular vibrations and non-radiant relaxation, fluorescence emission spectra from endogenous fluorophores consist of broad bands. Fluorescence spectra recorded from tissues are therefore complicated by overlapping bands from multiple constituent fluorophores. To gain diagnostic value, these complex spectra are corrected for system response, then analyzed or modeled using techniques such as multivariate linear regression, Monte Carlo simulation, and partial least squares discriminant analysis. The intensity of the fluorescence emission from pre-neoplastic and malignant tissues is generally lower than that from normal tissues.

Further, in biological media, fluorescence signals typically decay on nanosecond ($10^{-9}$ seconds) to sub-nanosecond time scales. Increased non-radiative decay leads to decreased quantum yield (ratio of the number of photons emitted to the number of photons absorbed), as well as decreased lifetime. Commonly used in vivo spectral readings do not take into effect the dynamics of fluorescent decay. Further, spectrally resolved measurements are inherently intensity dependant. Accordingly, there is a need for new screening methods and apparatuses which can effectively diagnose pre-malignant (pre-neoplastic) tissues and cells in vivo.

The present invention relates to an apparatus, called a Fluorescence Lifetime Spectrometer (FLS), which uses fluorescence lifetime spectroscopy. The FLS is capable of collecting the complete fluorescence emission spectrum and the transient decay of a selected spectral band simultaneously with data acquisition times less than one second. This rapid acquisition makes this technique clinically adaptable. The FLS is capable of accurately resolving fluorophore lifetimes from hundreds of picoseconds to tens of nanoseconds in duration, with an ultimate temporal resolution of 360 picoseconds. The resolution, sensitivity, range, and speed of the FLS are appropriate for detecting endogenous fluorophores in biological systems.

The FLS is a compact, portable instrument and may be used upon a three-shelf cart system, where one shelf holds a computer which may be used to control FLS detection parameters and data acquisition. A second shelf may be used to hold the optics and detectors. Vibration may be isolated from the cart via a spring platform. Power supplies and peripheral electronics may be located on a separate shelf. For clinical use, the two bottom shelves may be enclosed.

The present invention measures both the spectral and temporal fluorescence properties of tissue or cells. In simplest form, the apparatus of the present invention comprises a primary excitation light source; an optical fiber probe which delivers light to a remote tissue or cell sample and which collects resulting fluorescent emissions from the tissue or cell sample; a means of directing the returning fluorescent emissions from the sample to both spectral and temporal detections schemes; a spectrometer coupled intensified charge coupled device (ICCD) which detects fluorescent emissions from the tissue or cell sample and derives therefrom spectral fluorescence properties of the tissue or cell sample; a photodetector which detects temporal fluorescence emissions output from the sample; and a means connected to the photodetector for transiently digitizing a signal from the photodetector and deriving temporal fluorescence properties of the tissue or cell sample from the signal. The tissue or cell sample readings, are compared to readings of known tissue types, preferably known normal tissue or cell samples and/or known cancerous or precancerous tissue or cell samples to detect the presence of pre-cancerous or cancerous tissue or cells in the sample.

Figure 1:
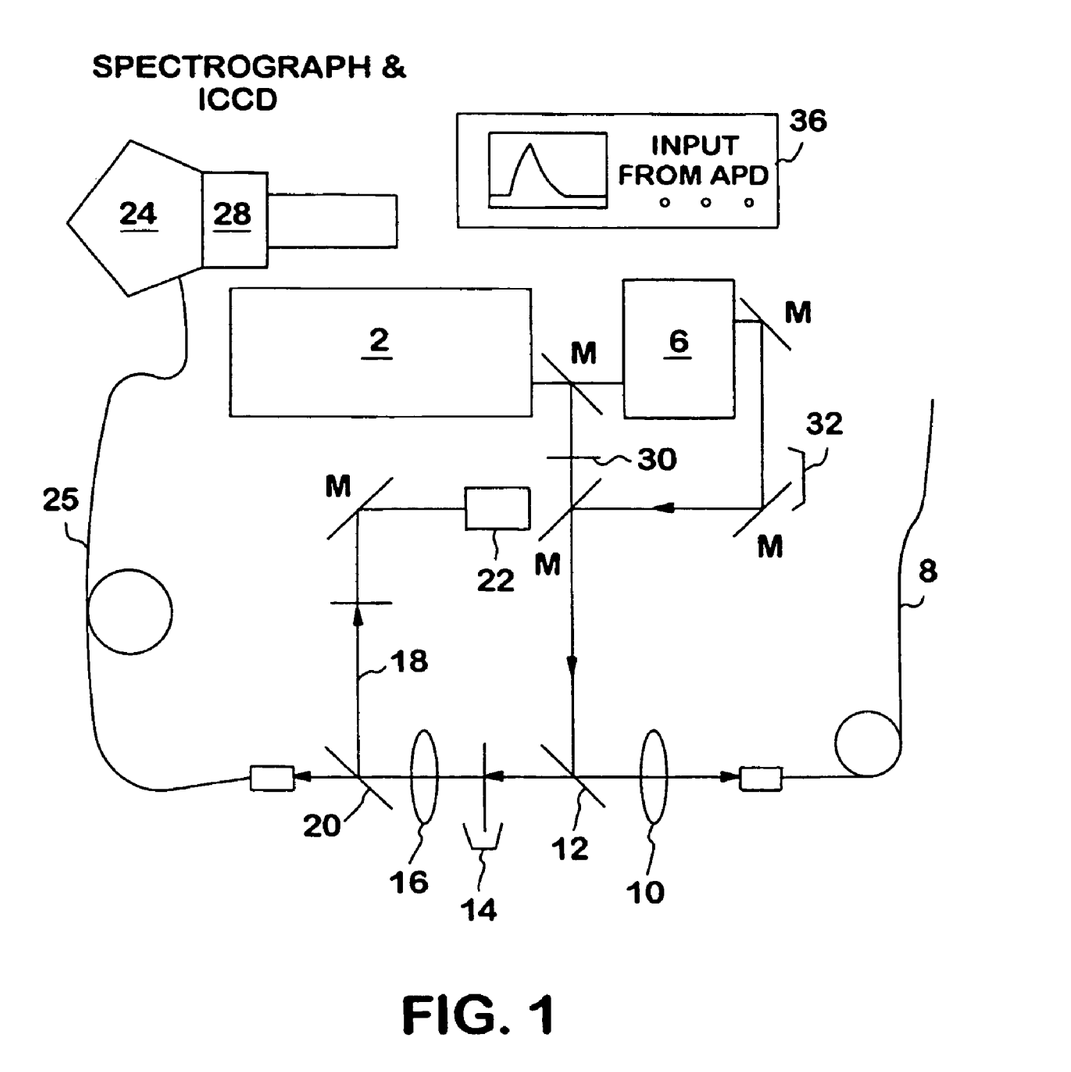
FIG. 1 shows a schematic of the FLS instrument.

In a preferred embodiment, as depicted in FIG. 1, the primary excitation light source 2 comprises a compact, pulsed nitrogen pump laser used as a fundamental 337.1 nm excitation source. However, as will be understood by one of skill in the art upon reading this disclosure, solid state lasers can also be used. This nitrogen pump laser has a pulsewidth of 4 ns and a spectral bandwidth of 0.1 nm. However, other lasers with pulsewidths $\leq 5$ nm and bandwidths $\leq 3$ nm can be used. The nitrogen pump laser, is preferably capable of operating between 1 and 20 Hz, and is typically run at 10 Hz, with a total pump energy of 144 µJ/pulse. The output of the primary excitation light source 2 is used for sample excitation by delivery of light through an optical fiber probe 8 to a sample. As shown, the primary excitation light source 2 may also be used for pumping a secondary excitation light source 6 comprising a separate dye laser module capable of producing pulses of laser light in the range 360-950 nm, with pulse widths of 4 ns, bandwidths of 3-10 nm, and an average energy per pulse of 40 µJ at 500 nm for sample excitation. The secondary excitation light source 6 output would be used for sample excitation by delivery of the light through an optical fiber probe 8 to a sample.

The selected excitation light 2, 6 is delivered into an optical fiber probe 8 by means of a wavelength specific dichroic mirror 12 and a lens 10. The dichroic mirror 12 is located in the pathway of the excitation light and directs the excitation light through an adjacently located lens 10 onto the optical fiber probe 8. The optical fiber probe 8 is preferably a quartz optical fiber probe, about 2.5 m long, 600 µm diameter. However, the probe may also comprise fiber bundles. Further, length and size of the probe can be varied to be compatible with the endoscope. When the laser light is 337.1 nm, it is preferred that the lens 10 be quartz. However, a glass lens can also be used for wavelengths longer than 400 nm. Further, as will be understood by those of skill in the art upon reading this disclosure, other means well known in the art for directing the returning fluorescent emissions from the tissue or cell sample to both the spectral and temporal detection schemes can also be used. In the embodiment of FIG. 1, the lens 10 and optical fiber probe 8 preferably have matched numerical apertures of 0.22. This fiber is used to deliver excitation light to the sample and to collect the resulting fluorescence emission from the sample. The lens 10 collimates the returning emission, as well as any scattered excitation light. The dichroic mirror 12 and an adjacent long pass filter 14 as shown in FIG. 1, may be used to eliminate residual excitation light, allowing only fluorescence emission to pass through the long pass filter 14. The fluorescence emission passing through the long pass filter 14 is then focused via an adjacent glass lens 16 and travels to a beam splitter 20. A portion of the fluorescence emission which passes through the beam splitter is transmitted onto a detection fiber 18, located adjacent to the lens and linked to the spectrometer coupled ICCD which detects fluorescent emissions output from the tissue or cell sample. The detection fiber and the beam splitter 20 are preferably quartz. However, for laser wavelengths greater than 400 nm, glass with reflective coating can also be used. Further, as will be understood by those of skill in the art upon reading this disclosure, other means well known in the art can also be used to transmit the fluorescence emission to the spectrometer coupled ICCD. In the embodiment of FIG. 1, a portion of the fluorescence is split off with a beam splitter 20 and directed toward a high-speed avalanche photodiode module 22 located adjacent to the lens 10 which receives and analyzes fluorescent emissions output from the tissue or cell sample. The fluorescence intensity as a function of time is detected by the avalanche photodiode module 22 and digitized on a connected oscilloscope 36. The oscilloscope analyzes a signal from the photodetector and derives the temporal fluorescence properties of the sample. The oscilloscope 36 is preferably a 1 GHz (5 GS/s) oscilloscope. Oscilloscopes with higher bandwidths can also be used. Further, as will be understood by those of skill in the art upon reading this disclosure, means other than an oscilloscope can be connected to the photodetector for transiently digitizing a signal from the photodetector and deriving temporal fluorescence properties of the tissue or cell sample from the signal. In the embodiment of FIG. 1, the temporal response of the high-speed avalanche photodiode module 22 is preferably optimized for detection from 400-1000 nm, with a rise time of about 300 ps, and a FWHM of about 500 ps. The portion of the fluorescence which is not split off from the detection fiber after passing through the long pass filter and adjacent glass lens travels through the detection fiber and is delivered to the entrance slit 24 of a spectrograph coupled ICCD 28. The spectrometer coupled ICCD analyzes the signal from the linked detection fiber and derives therefrom spectral fluorescence properties of the tissue or cell sample. The tissue or cell sample readings are compared to readings of known tissue types to determine the presence of pre-cancerous or cancerous tissues. As also shown in FIG. 1, neutral density filters 30 and 32 are placed in the excitation beam path and before the high-speed avalanche photodiode module to control fluorescence levels arriving at the sample and photodiode 22, respectively.

The spectrograph-coupled ICCD 28 collects the fluorescence emission in a single-shot, scan-free manner for fast data acquisition. For example, the ⅛ meter (F/3.7) spectrograph is preferably equipped with a 1200 line/mm grating blazed at 350 nm and a fixed entrance slit 24 of 200 μm. The ICCD camera head is preferably thermoelectrically cooled to −5° C. to help reduce dark noise associated with the CCD chip. The camera's CCD chip is preferably a 1024×128 μm pixel array, with an area per pixel of 26 μm$^2$. However, other CCD chips ranging from an array size of 1024×1 to a larger array and having a pixel area of 52 μm or smaller with suitable data acquisition speeds as noted above can be used. The chip, in combination with the spectrograph, produces a spectrometer wavelength resolution of 3 nm. Discrimination of the fluorescence signal from background lighting is critical. To accomplish this discrimination, the intensifier gate width is set to 100 ns. While the ICCD gate width is variable and could be set to values ranging from 3 ns to infinite duration (continuous operation), gate widths of about 100 ns are most effective at eliminating background light without reducing fluorescence emission intensity. Appropriate delays to compensate for light travel time and intensifier gating are produced using a delay generator, which effectively eliminates background radiation from interfering with the fluorescence spectrum acquisition.

The design of the nitrogen pump laser must account for pulse-to-pulse jitter, both in time and in intensity. In the case of the pump laser, the pulse-to-pulse energy stability specification is preferably ≦4% and the temporal jitter specification is ≦40 ns. For steady-state spectral detection, the ICCD camera accumulated signals and jitter would have no effect on the shape of the spectrum. The timing jitter in the output pulse of the nitrogen laser is accounted for by triggering the ICCD from the laser itself. For temporal detection, the oscilloscope is triggered from the high-speed avalanche photodiode module output, which only produces a trigger event when fluorescence light arrives on the high-speed avalanche photodiode module. This eliminates artifacts due to missed pulses or fluctuations in laser timing. To minimize effects on the averaged high-speed avalanche photodiode module signal due to pulse intensity fluctuations, the oscilloscope trigger level is set to a relatively high threshold greater than or equal to the top 20% of the fluorescence signal. This eliminates any nitrogen laser intensity fluctuations greater than 20% from being averaged into the recorded temporal decay.

Figure 2:
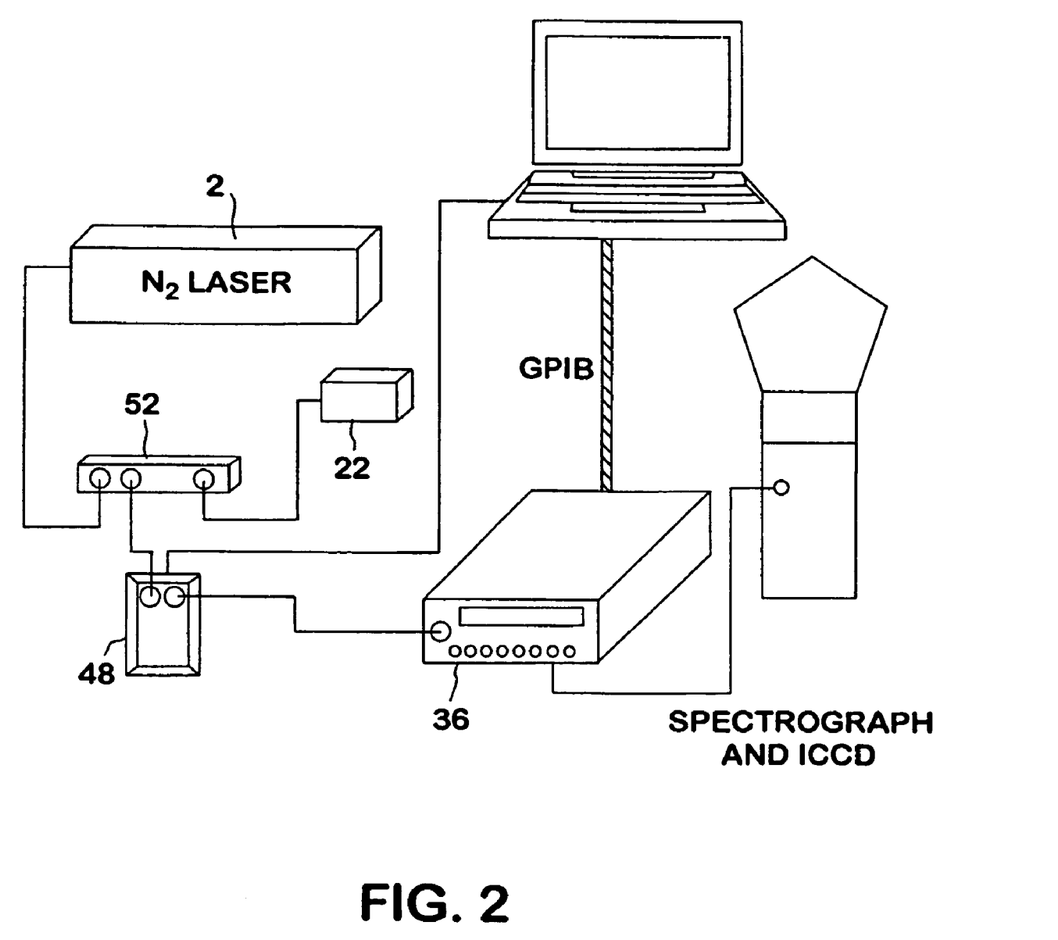
FIG. 2 shows a schematic of the FLS electrical system design. As shown in this schematic, the nitrogen laser provides an initiation pulse that is conditioned via a pulse conditioner containing a fast, monostable, multi-vibrator chip. This pulse is used to control the intensified charge coupled device (ICCD) gate timing via the delay generator.

In one aspect, the design of the FLS electrical configuration, as shown in FIG. 2, allows for external triggering of the ICCD gate and optimization of the gate timing to the arrival of the fluorescence. A near coincident electrical pulse on the main internal control board of the laser is used as an initiation trigger for the ICCD. However, this electrical trigger pulse may not be of the proper magnitude required by the ICCD multi-input/output box 48 (ICCD I/O Box in FIG. 2), which is +5 Volts transistor-transistor logic (TTL). Furthermore, it is highly susceptible to electrical ringing introduced by the spark-gap discharge of the laser. Hence, this sync-out is conditioned via a high-speed, monostable, non-retriggerable, multi-vibrator. This multi-vibrator will condition nominal electrical pulse into stable TTL pulse with a controllable width. This circuit is designated the Pulse Conditioner Circuit 52 in FIG. 2.

The pump laser may produce considerable electromagnetic interference and radio frequency emission (EMI/RF) noise that can interfere with optical detectors. This noise results from the discharge of the laser's internal high voltage power supplies. To reduce the EMI/RF noise, the laser may be enclosed in two Faraday cages that are electrically isolated from the system and from each other. The internal cage is constructed of copper mesh, the external cage is 2 mm thick aluminum, and all holes for cabling and light exit were kept to a maximum diameter of 15 mm. In addition, all signal and electrical cables should have a minimum of two layers of braided EMI shielding.

Unattenuated, the EMI/RF noise emitted by the laser may greatly interfere with the output signal of the High-speed avalanche photodiode module. To further isolate the high-speed avalanche photodiode module from the possible influx of EMI noise along cabling and DC power sources, the pulse conditioner circuit 52 is designed to operate as an electrical filter, and serves two purposes.

In one aspect, the pulse conditioner circuit conditions the sync-out of the nitrogen laser, as indicated above. The multivibrator, by the nature of its non-retriggerable operation, has the added feature that it filters the noise associated with the sync-out. This simple circuit adds a nominal temporal delay to the trigger pulse. Importantly, additional EMI filtering is achieved by introducing three wire wound ferrite coils into the circuit, which help to filter any EMI noise traveling along the center of the Bayonet Connector (BNC) cables. As the frequency increases, the noise peak-to-peak intensity decreases by a factor of 30 or more. The EMI/RF noise emitted from the nitrogen laser is measured to range above 100 MHZ, where the attenuation provided by the circuit is maximal. Thus, by using this circuit design, the noise propagating to the High-speed avalanche photodiode module is greatly attenuated.

In another aspect, the pulse conditioner circuit powers the High-speed avalanche photodiode module with a stable DC voltage (12.0±0.1 V). This can be achieved by using a small wall mount power supply which also supplies the power needed for the rest of the circuit. Outputs of this pulse conditioning circuit may be operated simultaneously or independently of each other. The ICCD is not affected by radiated electrical noise.

The software control program of the present invention is designed to be a graphical user interface (GUI) providing instrument parameter flexibility with simplified data collection. The GUI has two primary functions. First, the software controlled the thermoelectric cooling of the ICCD. This function included restricting data acquisition until a user-defined temperature is reached, monitoring and maintaining this temperature during data collection, and permitting controlled shutdown of the ICCD after use. This software function is necessary to prevent thermal stress on the image intensifier's output optical fibers. Without this control, shearing of these optical fibers from the silicon face-plate of the CCD might occur.

The software provides a user interface for FLS parameter adjustments and data acquisition. The software permits the ICCD to operate in a real-time mode that continuously and simultaneously displays the measured fluorescence emission spectrum and transient decay on-screen. This continuous mode operation, which is the default mode of the software, provides the user with an immediate gauge of signal levels and variability. For data acquisition using the FLS, the user clicks a graphical panel button, which changes the ICCD and oscilloscope to accumulate and average modes, respectively. Data from a user-defined number of laser pulses is then simultaneously gathered from the ICCD and oscilloscope. This information is then stored as an indexed ASCII file on the computer hard drive. Upon completion of data capture, the ICCD and oscilloscope are returned to continuous operation and the instrument is immediately prepared for the next measurement.

To enhance the flexibility of the FLS, ICCD parameters including the number of accumulated emission spectra, exposure time, and chip temperature are accessible through the GUI. The parameters of the oscilloscope or other transient digitizer may be changed manually on the instrument itself. While these parameters are easily incorporated into the software design, most can be eliminated to avoid unnecessary complication with the user interface. All graphical data outputs observed by the user are autoscaled to eliminate the need for physical adjustments to the FLS between measurements. The software package is designed to provide a user-friendly interface for the FLS without sacrificing the sensitivity and flexibility of the instrument.

A method for measuring spectral and temporal fluorescence properties of tissue simultaneously is also provided. According to this method an excitation light source is brought into contact with a tissue or cell sample and the tissue or cell sample is excited with the excitation light source to produce fluorescence from the tissue. The fluorescence emitted from the sample is collected and further detected with simultaneous spectral and temporal resolution.

The method of the present invention is useful in measuring the spectral and temporal properties of a tissue or cells and comparing these to measurements of healthy tissue or cells and/or diseased tissue or cells to determine the existing condition of the tissues. For example, in one embodiment, the method of the present invention can be used to detect precancerous and cancerous changes in tissues or cells in vivo. As demonstrated herein, changes in endogenous fluorescence such as NADPH and flavoprotein content may be detected spectrally and temporally and are indicative of precancerous or cancerous change. Accordingly, spectral and temporal fluorescent properties of a tissue or cell sample can be determined in accordance with the method of the present invention and can be compared to a normal, healthy tissue or cells and/or cancerous tissue or cells to identify any changes in endogenous fluorescence of the tissue of cell sample indicative of a precancerous or cancerous change.

Further, the apparatus has the ability to measure both endogenous and exogenous fluorescence, thus rendering it useful to monitor exogenous fluorescence in photodynamic therapy. Accordingly, the apparatus may be used to monitor drug uptake via detection of exogenous fluorescence, to monitor therapeutic intervention by photodynamic therapy via detection of endogenous and exogenous fluorescence, and to monitor therapeutic intervention with chemopreventative agents via detection of endogenous fluorescence.

Using the apparatus of the present invention, the tissue autofluorescence was examined as a method of non-invasive pre-neoplasia (pre-malignancy) detection in the lung. In these studies the intrinsic cellular autofluorescence from SV40 immortalized and distinct tobacco carcinogen-transformed (malignant) human bronchial epithelial cells was examined. These cell lines are useful models for studies seeking to distinguish between normal and pre-neoplastic human bronchial epithelial cells. The cells were characterized via spectrofluorimetry and confocal fluorescence microscopy.

For characterization via spectrofluorimetry, cell counts were held at approximately 300,000 cells per milliliter. This had the result of minimizing scattering and re-absorption artifacts in the fluorescence measurements. The spectrofluorimeter measurements described in Example 5 were used to record the excitation/emission matrices (EEMs) of BEAS-2B and BEAS-2B$_{NNK}$ cell suspensions. Excitation wavelengths were chosen approximately every 20 nm and ranged from 220 to 675 nm. Emission wavelengths ranged from 10 nm beyond the excitation wavelength to 800 nm. Artifacts from grating harmonics and/or ghosts were removed from the recorded data. The maximum intensities of the EEMs were normalized for comparison and the wavelengths limited for presentation clarity. Two dominant peaks were observed in both the BEAS-2B and BEAS-2B$_{NNK}$ cells. These two peaks occurred at 220/330 and 287/330 nm (excitation/emission wavelengths). These peaks corresponded closely with the peaks observed in the EEM of pure tryptophan (220/350 and 287/350 nm). The peak at longer wavelength excitation is reported to be the result of two closely spaced levels, the $^1L_a$ and $^1L_b$ of the indole moiety, while the shorter wavelength peak is the result of a higher electronic transition.

Excitation and emission spectra for pure tryptophan in PBS and BEAS-2B and BEAS-2B$_{NNK}$ cells in PBS were determined. The spectra were recorded at the maxima of emission or excitation, as determined by the corresponding EEM. The autofluorescence spectra recorded from both bronchial epithelial cell lines closely resembled the characteristic fluorescence of the amino acid tryptophan.

A minor autofluorescence feature observed in both the BEAS-2B and BEAS-2B$_{NNK}$ cell suspensions was observed with an emission maximum at 655 nm, upon excitation at 460 nm. This broad featureless emission (full width at half-maximum of 150 nm) was approximately forty times weaker than that from the emission band at 330 nm. To investigate the origin of this emission, the excitation spectrum was recorded (610 nm emission) between 325 and 600 nm. This range was chosen based on values expected for porphyrins and lipofuscin, two possible endogenous fluorophores roughly corresponding to the observed emission. No distinct excitation feature corresponding to reported endogenous fluorophores was found in this range.

No appreciable difference in autofluorescence emission intensity was noted between the BEAS-2B and BEAS=2B$_{NNK}$ human bronchial epithelial cells for either the tryptophan or the 655 nm band. In addition, spectrofluorimetry revealed no emission from other common endogenous fluorophores, such as NADH and flavins. This was presumably due to the low sensitivity of the LS-50 spectrofluorimeter. In recent studies on human cervical epithelial cell suspensions, tryptophan emission was found to be at least two orders of magnitude higher than the fluorescence emission from either NADPH or FAD (Richards-Kortum et al. Optical Society of America Technical Digest 2000: 209-211). To measure the weaker emission of other endogenous cellular fluorophores, sensitive confocal fluorescence imaging methods were employed.

In confocal fluorescence microscopy, a Leica confocal microscope was used to measure the autofluorescence of individual BEAS-2B and BEAS-2B$_{NNK}$ cells. This highly sensitive spectrophotometer coupled instrument allowed for the detection and spatial localization of distinct fluorophore species and excluded any appreciable contribution from other species, via tunable wavelength discrimination. Two differential interference contrast (DIC) images of BEAS-2B cells were determined with corresponding overlays of pseudo-color confocal fluorescence images. The images were collected using an excitation wavelength of 351 nm and emission intensity integration between 426 and 454 nm. The images revealed granular cytoplasmic autofluorescent structures with excitation/emission characteristics that corresponded closely with known NADH values. These images were compared to images from the same cells excited at 488 nm, with the resulting emission integrated between 530 and 555 nm. The emission in this wavelength range was consistent with the presence of flavins in the cells. From these images, it is apparent that the instrument was capable of detecting emission from these weakly fluorescing endogenous species present in human bronchial epithelial cells.

Confocal autofluorescence images of BEAS-2B and BEAS-2B$_{NNK}$ cells were compared. Emission was consistent with both NADH (excitation wavelength at 351 nm, emission integrated between 426-454 nm) and flavins (excitation wavelength at 488 nm, emission integrated between 530-555 nm) for the BEAS-2B and (BEAS-2B$_{NNK}$ cells. DIC images of the corresponding fields were used for reference. All microscope and laser parameters were held constant between corresponding images, which were acquired within minutes of one another. New areas were imaged on each sample to avoid photobleaching, and optical sections were chosen to be similar by focusing on nucleoli. These images indicate that the tobacco carcinogen-transformed BEAS-2B$_{NNK}$ cells exhibited reduced NADH and flavin emission as compared to the immortalized BEAS-2B human bronchial epithelial cells. In addition, the punctate cytoplasmic fluorescent granules present in the immortalized cells appeared to be more dispersed in the carcinogen-transformed cells than in parental BEAS-2B cells.

The changes in cellular autofluorescence between immortalized and carcinogen-transformed human bronchial epithelial cells provide evidence of the utility of the apparatus and method of the present invention in noninvasively diagnosing pre-neoplasia in lung tissue using fluorescence spectroscopy and imaging.

Clinical in vivo operability of the FLS was also demonstrated during bronchoscopies and lung tumor resection. The in vivo FLS measurement protocol facilitated dual wavelength excitations of 337.1 nm and 450 nm, with steady state emission collected from 390 nm to 620 nm and fluorescence lifetime emission limited to 430 nm±50 nm or 550 nm±50 nm(fwhm) based upon the APD bandpass filter. Laser power was limited via quartz neutral density filters and measured prior to each set of experiments for intensity normalization. Similarly, the fluorescence light fluence arriving at the APD was limited to less than 500 mV using glass neutral density filters. The steady-state background and the instrument response were collected for correction of the steady state and temporal autofluorescence. Neoplastic appearing tissue was measured a minimum of three times while simultaneously collecting the steady-state and time-resolved autofluorescence. The fiber was removed from the tissue surface and replaced between each measurement. Normal appearing tissue was measured in a similar manner. Following each set of measurements the interrogated tissue (abnormal and normal) was biopsied for histopathological analysis. All fibers were steam sterilized for 30 minutes prior to clinical use.

Figure 4A:
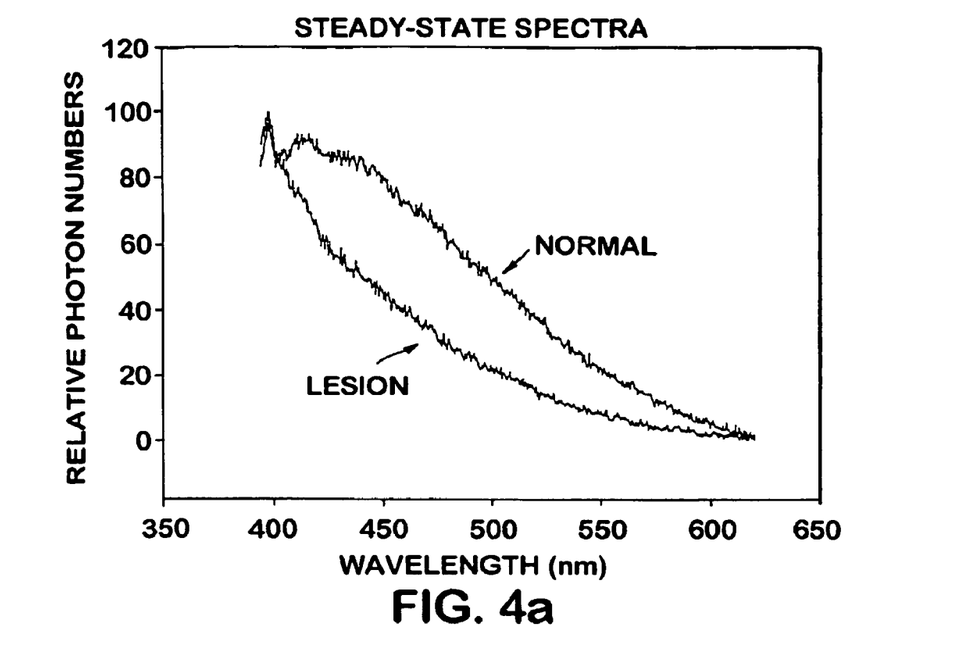
FIGS. 4(a) and 4(b) provide exemplary 337.1 nm excited, steady-state (FIG. 4a) and time-resolved (FIG. 4b) tissue autofluorescence curves normalized to peak values for both normal and abnormal lung tissue.
Figure 4B:
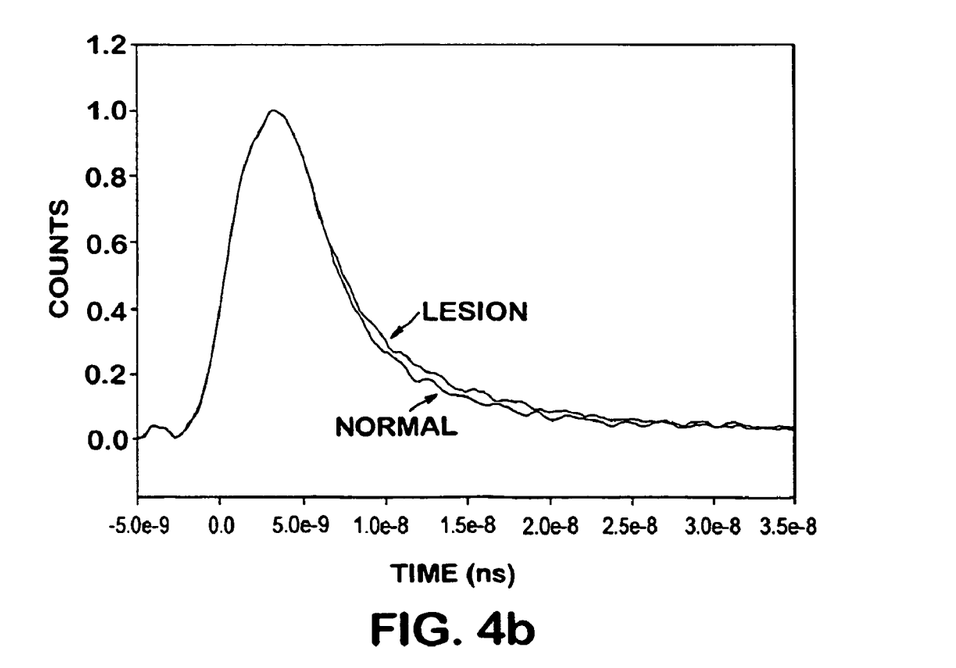

In vivo FLS measurements were obtained during routine rigid bronchoscopy. The location of the abnormal lesion was identified via white-light video bronchoscopy. The 600 μm diameter fiber of the FLS was then inserted through the instrument channel of the bronchoscope and brought into gentle contact with the tissue. Measurements, as described above, were collected at both excitation wavelengths. No bleeding of the tissue was observed. The fiber was then removed from the instrument channel and a biopsy of the area probed by the fiber was collected. The entire scope was then withdrawn by approximately two inches and the fiber was reinserted into the rigid bronchoscope. The fiber was placed into gentle contact with the wall of the normal appearing trachea and the same measurement protocol was repeated. A biopsy of this normal appearing area was also obtained. The entire measurement and biopsy regimen took no more than five minutes to complete. FIG. 4 shows an example of the 337.1 nm excited, steady-state (FIG. 4a) and time-resolved (FIG. 4b) tissue autofluorescence curves normalized to peak values which were generated in these in vivo measurements.

The steady-state fluorescence emission spectrum depicted in FIG. 4a of normal tissue shows a peak centered near 440 nm, consistent with NADPH. The portion of the curve in the bluest wavelength range is believed to result from collagen emission. The steady-state autofluorescence from the lesion was found to generally decrease in intensity relative to the normal tissue. Further, relative to collagen, the contribution from the NADPH structure was lower in the lesion than in normal tissue. FIG. 4b illustrates that the average fluorescence lifetime of the normal tissue was slightly lower than that of the lesion: 3.6±0.1 nanoseconds vs. 4.4±0.1 nanoseconds. This is consistent with the observed spectral differences between normal and lesion tissues, because the spectra indicate that, relative to collagen, there is more NADPH emission from normal tissue than from the lesion and, because NADPH has a much shorter lifetime than collagen, the normal tissue would be expected to have a shorter average lifetime than the lesion.

The fact that relatively large spectral differences between normal and lesion were detected, while lifetime differences between the two were not so pronounced may be consistent with the fact that the lesion in question was diagnosed by histopathology as a benign papilloma, and was not a malignant tumor. Thus, even though the lesion's morphology is clearly different from normal tissue, resulting in spectral distortions induced e.g. by optical scattering artifacts, in this case the lesion's biochemistry may be closer to normal tissue, resulting in relatively similar tissue lifetimes. Fluorophore lifetimes are, in general, insensitive to factors such as absorption and scattering that may strongly influence fluorescence intensities.

The following non-limiting examples are provided for illustrative purposes and are not intended to limit the scope of the present invention.

EXAMPLES

Example 1

Calibration and Data Analysis

The FLS was calibrated spectrally for both wavelength and absolute fluorescence intensity. Wavelength calibration was achieved using a Hg(Ar) lamp (Model 6035, Oriel Instruments, Stratford, Conn. USA) by reference to known emission lines. Calibration of the FLS wavelength was performed for three overlapping wavelength ranges (250-450 nm, 400-600 nm, and 450-650 nm), as determined by the spectrograph grating. Correction for the FLS spectral instrument response was achieved by dividing measured spectra with a wavelength dependent sensitivity factor, $S(\lambda)$. $S(\lambda)$ was calculated by measuring the irradiance, $M_{Lamp}(\lambda)$, from a NIST traceable tungsten halogen lamp (#63355 S.N. 7-1329, Oriel Instruments, Stratford, Conn. USA) and dividing this spectrum by the known theoretical spectrum, $T_{Lamp}(\lambda)$, provided by the manufacturer, $$S(\lambda)=(M_{Lamp}(\lambda))/(T_{Lamp}(\lambda))$$

All measurements and theoretical spectra were converted from units of energy to absolute photon numbers (quanta), creating a unitless $S(\lambda)$. By determining $S(\lambda)$ in this way, the collection of distortion-free emission intensity spectra measured in photon numbers was possible, as discussed below. The time-domain instrument response of the FLS included distortions introduced by the laser excitation pulse duration and the response of the electronics. It was measured using excitation light at 337.1 nm to induce fluorescence emission at 560 nm from $10^{-6}$M Rose Bengal in deionized water. Rose Bengal in deionized water was well suited for determining the FLS instrument response for two reasons. First, it is a fast emitting fluorophore with a lifetime of approximately 90 ps, which is beyond the temporal resolution of the FLS device. Second, its emission wavelength is consistent with that of typical endogenous fluorophores found in biological systems. The instrument response function determined in this way had a FWHM of 4.5 ns.

Measured fluorescence spectral data were corrected for solvent contributions by background subtraction of a pre-recorded solvent emission spectrum, and for the non-uniformity of the instrument response by division with the wavelength dependent sensitivity factor $S(\lambda)$. Thus, $$\text{Corrected Emission} = \frac{M(\lambda) - B(\lambda)}{S(\lambda)}$$

where $M(\lambda)$ is the measured sample emission and $B(\lambda)$ is the background emission. $M(\lambda)$ and $B(\lambda)$ were measured in units of CCD counts per nanometer, a linear measure of photon numbers arriving at the detector, and $S(\lambda)$ was unitless. The spectra collected were the result of accumulating the fluorescence emission resulting from 10 or more individual laser pulses, ensuring good signal to noise ratios (SNR). Spectral calibration was tested by recording the emission from the fluorescence standard quinine sulfate and data is depicted in the following Table.

| Wavelength (nm) | Lakowicz Data (a.u.) | FLS Measured Data (a.u.) |
| --- | --- | --- |
| 310 | 0 | — |
| 350 | 4 | — |
| 380 | 18 | — |
| 400 | 151 | 75 |
| 410 | 316 | 206 |
| 420 | 538 | 444 |
| 430 | 735 | 660 |
| 440 | 888 | 807 |
| 445 | 935 | 894 |
| 450 | 965 | 972 |
| 455 | 990 | 993 |
| 457.2 | 1000 | 998 |
| 460 | 998 | 984 |
| 465 | 979 | 951 |
| 470 | 951 | 909 |
| 475 | 916 | 868 |
| 480 | 871 | 844 |
| 490 | 733 | 740 |
| 500 | 616 | 600 |
| 520 | 408 | 381 |
| 550 | 171 | 173 |
| 600 | 19 | 30 |
| 650 | 3 | — |
| 700 | 0 | — |

The spectrum is in good agreement with known literature values, shown as solid circles.

Fluorescence decays were analyzed by least-squares iterative reconvolution using the Marquardt algorithm (Light Analysis, Quantum Northwest, Inc.) to account for instrument response and to extract lifetimes and amplitudes. The analysis program was written for use with data obtained via time-correlated single-photon counting methods. Therefore, it was modified to include the uniform weighting of residuals appropriate for the analog signal statistics of the FLS. Transient decays measured with the FLS, M(t), were interpreted as being the convolution of the true or intrinsic fluorescence decay, F(t), and the instrument response function, I(t), described above $$M(t)=F(t)*I(t) \qquad (3)$$

Intrinsic decays were modeled as multi-exponential decays $$F(t) = \sum_I \alpha_i \exp\frac{-t}{\tau_i}$$

with lifetimes $\tau_i$ and amplitudes $\alpha_i$. Thus, the normalized area under the intrinsic decay curve due to component I (or, the percentage contribution of component I to the overall fluorescence intensity) was given by $$Area_i = A_i = \frac{\alpha_i \tau_i}{\sum_I \alpha_i \tau_i}$$

Example 2

Instrument Characterization for Spectrally-Resolved Detection

FLS spectral resolution, determined by measuring the FWHM of the 507.3 nm·line of the Hg(Ar) lamp, was found to be 3 nm, which is sufficient to resolve the relatively broad spectral bands associated with endogenous biological fluorophores. FLS spectral sensitivity was determined by measuring the SNR of the fluorescence emission from varying concentrations of fluorescein dye molecules in ethanol. Samples in the study ranged from $10^{-4}$-$10^{-7}$ M in concentration. For each sample, the total fluorescence emission induced by forty laser pulses (337.1 nm; 0.35 µJoules/pulse) was accumulated by the ICCD, with the intensifier gain set to a value of two. The following Table summarizes these results.
Spectrally Resolved Fluorescence Intensity Signal-to-Noise Ratio (SNR) vs. Fluorescein Dye Concentration in Ethanol

| Dye Concentration (M) | SNR |
|---|---|
| $1 \times 10^{-4}$ | $1.9 \times 10^4$ |
| $1 \times 10^{-5}$ | 1230 |
| $1 \times 10^{-6}$ | 105 |
| $5 \times 10^{-7}$ | 29 |
| $2.5 \times 10^{-7}$ | 16 |
| $1 \times 10^{-7}$ | 7 |

At the highest concentration the SNR was $1.9 \times 10^4$ and at the lowest concentration the SNR was 7. Reasonable, minimum SNR values for studies with the FLS would ideally be no less than 25, corresponding to a detectable concentration level less than $5 \times 10^{-7}$ M. Thus, as designed, the FLS is a highly sensitive instrument capable of detecting minute fluorophore concentrations in non-scattering media. This sensitivity was sufficient to detect endogenous fluorophore concentrations in turbid biological systems, as described below.

The spectral dynamic range (DR) of the FLS was calculated from $$DR = \frac{S_{max} - N}{N}$$

where $S_{max}$ was the maximum signal level achievable without ICCD saturation and N was the noise level recorded with the intensifier gain set to a typical value of two. The spectral dynamic range of the FLS was determined in this way to be 3 decades. The spectral range of the FLS was limited by the long pass filter (FIG. 1) and the spectrograph grating to be 350-800 nm.

Measured fluorescence lifetimes (337.1 nm excitation) for standard fluorophores in solution compared with literature values from time-correlated single-photon counting experiments are depicted in the following table. (The reported error is the standard deviation over repeated measurements.)

| Fluorophore (a) | Measured Lifetime (ns) | Measurd Error (ns) | Literature (c) Lifetime (ns) | Literature (c) Error (ns) |
|---|---|---|---|---|
| Rose Bengal in methanol | 0.682 | 0.023 | 0.540 | |
| Rose Bengal in methanol | 0.821 | 0.023 | 0.600 | |
| Rose Bengal | 0.859 | 0.024 | 0.850 | 0.030 |
| Rose Bengal | 0.843 | 0.030 | | |
| Rhodamine 610 in H$_2$O | 1.67 | 0.030 | 1.52 | 0.050 |
| Rhodamine 610 in H$_2$O | 1.86 | 0.080 | | |
| Rhodamine 610 | 3.01 | 0.220 | 2.6, 2.85 | 0.050 |
| Rhodamine 610 (b) | 3.56 | 0.100 | 2.79 | 0.050 |
| 9-cyanoanthracene | 11.7 | 0.420 | 11.85 | 0.030 |
| 9-cyanoanthracene[b] | 14.4 | 0.440 | 14.76 | |
| 9-CA/R610 Mix | $\tau_1 = 2.25$ | 0.390 | | |
| | $\tau_2 = 12.7$ | 0.400 | | |

(a) $<5 \times 10^{-6}$ M in ethanol, unless specified
(b) degassed with argon for 20 minutes
(c) J. R. Lakowicz, Principles of Fluorescence Spectroscopy 1999.

As discussed above, fast emitting fluorophores, like Rose Bengal, with lifetimes ranging in the hundreds of picoseconds could be reliably measured. Measurements on Rhodamine 610 (Exciton, Dayton, Ohio USA) demonstrated the ability of the FLS to accurately monitor nanosecond and sub-nanosecond fluorescence lifetimes. This time regime is important to FLS applications, because biologically relevant fluorophores are known to emit on these time scales. To test the ability of the FLS to measure long fluorescence lifetimes, measurements on 9-cyanoanthracene (15,276-5 Aldrich., Milwaukee, Wis. USA) in ethanol, with a lifetime value of 14.76 ns, were made. The FLS measured lifetime of 14.4±0.44 ns was in good agreement with the previously reported data shown in preceding Table. All errors reported were standard deviations over repeated measurements.

Finally, the FLS was used to predict fluorophore lifetimes of a mixture of 9-cyanoanthracene and rhodamine 610. As expected, the decay from the mixture was best fit by a bi-exponential decay function, with lifetimes of 12.7±0.40 and 2.25±0.39 ns. These values were in reasonable agreement with the lifetime values of the individual fluorophores, 11.7±0.42 and 3.01±0.22 ns.

All compounds and solvents were used directly from the manufacturer without further purification. In addition, the pH and temperature conditions employed here often differed from those in the reported literature. These factors, in combination with the finite number of data points accumulated by the rapid acquisition FLS relative to lengthy and data-rich TCSPC methods, contributed to the lifetime error and deviation versus literature values. Overall, the sensitive FLS provided a reliable and reproducible measure of fluorescence lifetimes with one second data acquisition times, and was thus found to be well suited for the measurement of endogenous fluorescence lifetimes in biological systems.

Example 3

Application to Study Systems

The FLS instrument designed, calibrated and characterized above was applied to study systems of interest in biology and medicine. For all of the studies described here, the excitation laser wavelength was 337.1 nm and the excitation laser energy was held below 20 µJ/pulse. This value of nitrogen laser energy was recently determined to be a threshold below which artifacts due to photobleaching were minimized in studies on biological systems. Indeed, no effects due to photobleaching were observed in the measurements described below. Thus, these experimental conditions reflect FLS system parameters to be used in future biomedical applications of the instrument.

The FLS instrument was employed to measure fluorescence lifetimes and amplitudes of several biomolecules known to be present in human cells and tissues, as summarized in the following Table.

Measured fluorescence lifetimes and amplitudes for endogenous biological fluorophores in vitro (337.1 nm excitation), with comparison to literature values are depicted in the following Table.

resolved data were system response corrected and fit to multi-exponential decays to extract lifetimes and amplitudes, as described above. A minimum of ten independent measurements were made for each sample and averaged. Results of the analysis and comparisons with literature values are presented in Table 3. Wide ranges of lifetime values reported in the literature are common with complex biomolecules. The FLS results presented herein are within the reported ranges and thus are in good agreement with the literature.

The simultaneous spectral and temporal resolution of the instrument was demonstrated by the representative measurement for NADH. Excitation and emission conditions were as reported for Table 3, thus demonstrating the ability of the FLS to accurately resolve sub-nanosecond lifetimes of biological fluorophores.

The FLS instrument was designed to have the sensitivity, speed, and portability required for use in the clinic. In order to demonstrate this capability, the instrument was employed to measure endogenous fluorescence from human skin tissue in vivo. To perform the measurement, the fiber optic probe first was brought into gentle contact with skin on the inside of the forearm. Ten pulses of excitation light at 337.1 nm (4 µJ/pulse) were then delivered to the skin via the fiber optic probe, and the resulting endogenous fluorescence was col-

| Fluorophore <5 × 10⁻⁶ M in PBS | Measured Lifetime | | Measured Area | | Literature Lifetime | | Literature Area | | References |
|---|---|---|---|---|---|---|---|---|---|
| | $T_1$ | $T_2$ | $A_1$ | $A_2$ | $T_1$ | $T_2$ | $A_1$ | $A_2$ | |
| Tryptophan | 0.54 | 4.45 | 0.33 | 0.66 | 0.62 | 3.20 | 0.22 | 0.78 | 1 |
| | | | | | 0.53 | 3.10 | 0.33 | 0.67 | 2 |
| | | | | | 1.47 | 2.78 | 0.72 | 0.28 | 3 |
| Elastin | 1.63 | 7.36 | 0.36 | 0.64 | 1.7 | 8.3 | | | 4 |
| | | | | | 1.3 | 5.8 | | | 4 |
| | | | | | 1.4 | 6.7 | 0.58 | 0.42 | 3 |
| | | | | | 1.12 | | 0.27 | 0.73 | 5 |
| | | | | | 6.57 | | | | |
| FAD | 2.63 | | | | 2.3 | | | | 6 |
| | | | | | 2.85 | | | | 5 |
| NADH (free) | 0.36 | | | | 0.3 | | | | 7 |
| | | | | | 0.26 | | | | 8 |
| | | | | | 0.66 | | 0.77 | 0.23 | 3 |
| | | | | | 0.24 | | | | 6 |
| | | | | | 0.58 | | | | |
| | | | | | 0.4 | | 0.97 | 0.03 | 5 |
| | | | | | 0.38 | | | | |
| | | | | | 1.38 | | | | |

[1] J. Petrich, M. Chang, D. McDonald, G. Fleming, Journal of the American Chemical Society, 105, 3824-3832 (1983).
[2] A. Szabo, D. Rayner, Journal of th American Chemical Society, 102, 554-563 (1980).
[3] S. Andersson-Engels, J. Johansson, K. Svanberg, S. Svanberg, Photochemistry and Photobiology, Vol. 53, No. 6, pp. 807-814 (1991).
[4] J.-M. Maarek, W. J. Snyder, W. S. Grundfest, SPIE, 2980, 278-285 (1997)
[5] M.-A. Mycek, K. Vishwanath, K. T. Schomacker, N. S. Nishioka, Optical Society of America Technical Digest, 11-13 (2000)
[6] J. R. Lakowicz, Principles of Fluorescence Spectroscopy (Second Edition) New York, Kluwer Academic/Plenum (1999)
[7] K. Konig, M. W. Berns, B. J. Tromberg, Journal of Photochemistry and Photobiology, B, 37, 91-95 (1997)
[8] L. Pfeifer, K. Schmalzigaug, R. Paul, J. Lichey, K. Kemnitz, F. Fink, SPIE, 2627, 129-135 (1995).

Figure 3A:
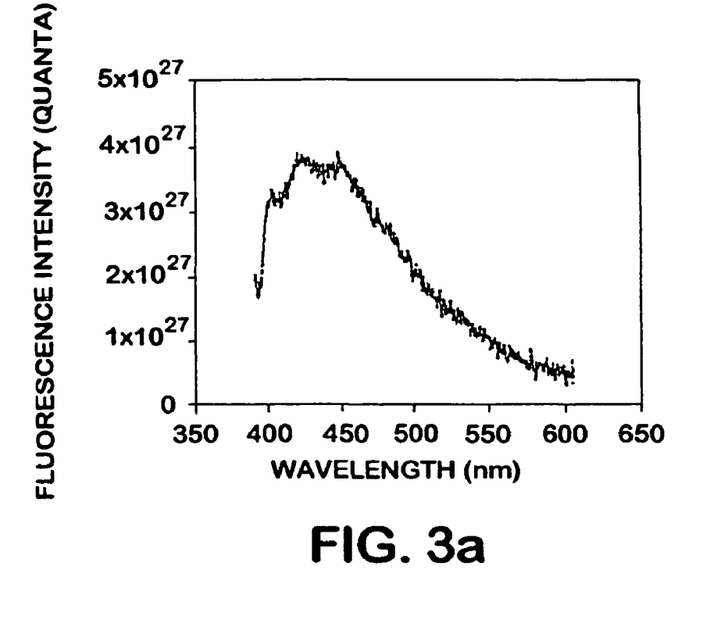
FIGS. 3a and 3b show instrument response corrected steady state (FIG. 3a) and time-resolved (FIG. 3b) (shown by dotted line) endogenous fluorescence emissions from human skin (337.1 nm excitation). The measurement was made using a fiber optic probe placed on the inside of the forearm and data was acquired in 1 second.
Figure 3B:
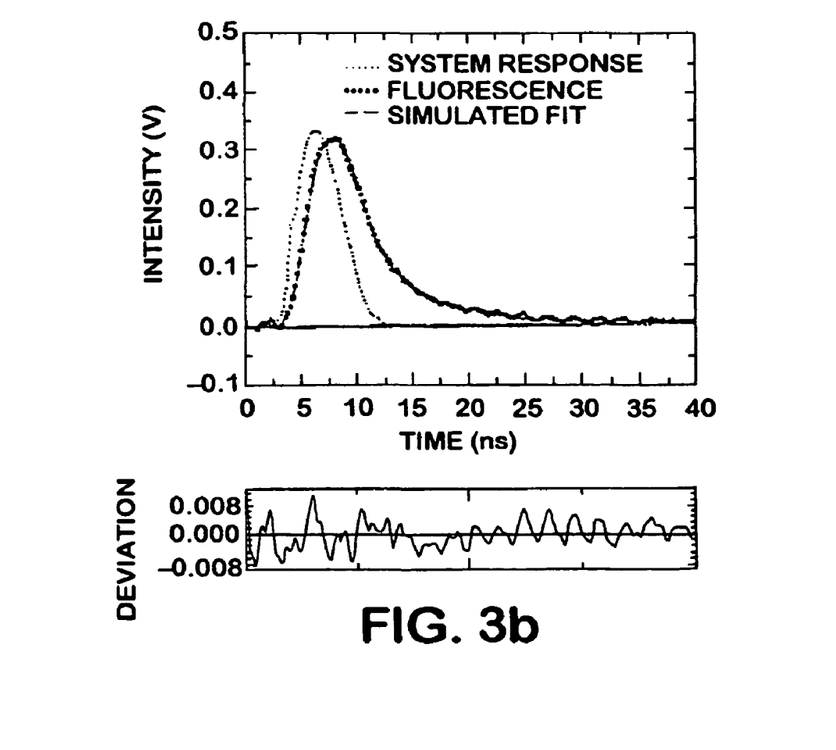

For the study, NADH and flavin adenine dinucleotide (FAD) were dissolved in phosphate buffered saline (PBS) (21-040-CV Lot 21040039, Cellgro, Herndon, Va. USA) to concentrations less than 5×10⁻⁶ M. Tryptophan (T-0254, Lot 29H0710, Sigma, St. Louis, Mo.) and elastin (from bovine neck ligament, E-1626, Lot 35H710, Sigma, St. Louis, Mo. USA) were wetted with PBS. Samples were then placed in quartz cuvettes (Type 3, NSC Precision Cells Inc., Farmingdale, N.Y. USA) and the fiber optic probe from the FLS was brought into contact with the sample. Each measurement used 10-15 pulses of excitation light, giving a data acquisition time for each measurement of less than one second. Timelected by the same probe and detected with simultaneous spectral and temporal resolution. A bandpass filter centered at 460±5 nm was placed before the High-speed avalanche photodiode module. Fluorescence spectra were accumulated and fluorescence decays were averaged over the 10 pulses, with a total data acquisition time less than 1 second. Results of the measurements are presented in FIG. 3. FIG. 3(a) shows a broad spectrum consistent with structural protein fluorescence and FIG. 3(b) shows the time-resolved measurement (dotted line) and fit (solid black line) to a double exponential decay with $\tau_1$=0.938 ns ($A_1$=0.40) and $\tau_2$=5.3 ns. These measurements show spectral bands attributed to collagen fluorescence (modified by hemoglobin absorption). In vivo fluorescence measurements are influenced by absorption and scattering in tissues, and the FLS was sensitive enough to detect differences in scattering and absorption due to differing melanin content in skin (data not shown). Time-resolved traces obtained in vivo with the FLS revealed excellent signal-to-noise characteristics with relatively little excitation energy per pulse (well below known photobleaching thresholds) and a narrow bandpass filter before the High-speed avalanche photodiode module for high spectral selectivity.

The properties make this apparatus readily adaptable to clinical diagnostic and therapeutic purposes.

Example 4

Human Bronchial Epithelial Cell Lines

The cells studied were previously described and included a line (designated BEAS-2B) derived from normal human bronchial epithelial cells that was immortalized via transduction of the SV40 T antigen (Reddel et al. Cancer res. 1988 48:1904-1090. Another line (designated BEAS-2B$_{NNK}$) was derived through tobacco-carcinogen induced transformation of BEAS-2B cells following treatment with N-nitrosamine-4-(methylnitrosamino)-1-(3-pyridyl)-1-butanone (NNK) (Langenfeld et al. Oncogene 1996 13:1983-1999). BEAS-2B cells retain features of normal human bronchial epithelial cells, but can be continuously passaged in vitro. The tobacco carcinogen-transformed BEAS-2B$_{NNK}$ line has acquired characteristics of malignant bronchial epithelial cells including tumorigenicity in athymic mice and enhanced anchorage independent growth. These cell lines have proven useful for identifying carcinogenic and anti-carcinogenic pathways. These lines represent valuable models for studies seeking to distinguish between immortalized and transformed human bronchial epithelial cells.

For cell suspension studies, monolayer cultures maintained in a chemically defined medium, LHC-9, (Biofluids, Rockville, Md.) at 37° C. and 5% $CO_2$, were trypsinized (0.05%) for 4 minutes, diluted in medium, and centrifuged for 4 minutes. Upon removal of the medium, cells were washed and re-suspended in phosphate buffered saline (PBS), before being placed in a 1 cm quartz cuvette. All measurements were made in less than one hour after re-suspension to preserve cell viability. Viability limits were determined by measuring the occurrence of fluorescence changes over time. These changes were found to be negligible within this one-hour period.

For imaging experiments, non-confluent monolayers of cells were prepared on standard cover slips by plating cells 24 hours prior to imaging. For each cell line, three independent cell cultures were maintained. From each culture, a minimum of two glass cover slips were used. The cover slips were moved from the incubator directly to the microscope, where multiple measurements were taken. All images were taken in culture medium. Visual inspection demonstrated that the presence of media increased the viability of the cells to greater than one hour. No sample was imaged for more than 45 minutes.

Example 5

Spectrofluorimetry

Spectrofluorimetry measurements were performed on the model systems described above to characterize their autofluorescence properties. A Perkin-Elmer LS-50 Dual Monochromator Luminescence Spectrometer was used for fluorescence measurements throughout the ultraviolet, visible, and near-infrared regions of the electromagnetic spectrum. The instrument contained a Xenon-arc discharge lamp as an excitation light source and a red-enhanced photomultiplier tube (Hamamatsu R928), with an extended range of 200-900 nm, as an emission detector. Emission was collected at a 90-degree angle relative to the excitation light path. The wavelength accuracy of the instrument was ±1.0 nm, and the reproducibility was ±0.5 nm. All spectra were corrected for solvent contributions, by background subtraction of a pre-recorded solvent emission, and for the non-uniformity of the instrument response, by division of a wavelength dependent sensitivity factor. These sensitivity factors were previously obtained, for this spectrometer, by recording the fluorescence emission of quinine sulfate (0.1N) and forming the ratio with the known standard spectrum. Equation 1 describes the spectral correction procedure:

$$\text{Corrected Emission} = [M(\lambda) - B(\lambda)]/[S(\lambda)] \quad (1)$$

where $M(\lambda)$ is the measured sample emission and $B(\lambda)$ and $S(\lambda)$ are the background and sensitivity factors. Photobleaching of the cell suspension was not observed, as determined by rescanning several spectra at the completion of each experiment. All measurements were made a minimum of three times, using new cell cultures each time.

Importantly, it was found that high cell counts can lead to appreciable spectral artifacts, including intrusive harmonic peaks and intensity fluctuations. The origin of these artifacts is presumably due to increased scattering of the excitation light as well as increased re-absorption of the fluorescence emission. Therefore to determine an acceptable cell count range for recording fluorescence spectra, we measured the BEAS-2B emission intensity (of a band consistent with the amino acid tryptophan) as a function of the cell number density. For cell counts ranging from 60,000 to approximately 500,000 per milliliter, the emission intensity increased nearly linearly. Beyond this range, the curve deviated from this trend, presumably due to re-absorption and scattering effects. While the observed linearity in the 60,000 to 500,000 cells per milliliter region was not perfect, the spectra recorded in this range were sufficiently free from the spectral artifacts noted at higher cell counts. The source of deviation from linearity arises from both the above mentioned effects and error associated with cell counting. For the experiments reported here, cell counts were consistently held at a level of approximately 300,000 cells/ml, as determined by hemocytometry.

Example 6

Confocal Fluorescence Microscopy

Fluorescence imaging experiments were performed on a Leica confocal spectrophotometer (Model TCS SP) equipped with an upright Leica research microscope and the necessary optics for differential interference contrast (DIC) and conventional epi-illumination. The images presented here were collected with a 63×, 1.32 N.A. planapochromatic objective and a 0.9 N.A. condenser. The confocal system employed fiber-coupled UV, argon, krypton-argon, and helium-neon lasers, providing excitation sources at wavelengths 351, 364, 488, 514, 568, and 633 nm. Imaging occurred via transmitted and fluorescent light detection, the latter via a tunable spectrophotometer instead of filter cubes. The continuously variable spectrophotometer allowed the user to determine the emission spectrum of a given fluorescent signal and to limit fluorescence collection to a precise emission range. This feature ensured that autofluorescence from living cells could be selectively scanned to identify the contributing wavelengths and that accurate fluorophore specific images could be obtained. For the images presented here, cells were excited sequentially with two wavelengths (351 nm and 488 nm), rather than simultaneously, thus eliminating potential signal crossover between recording channels. The emission wavelength ranges detected were 426-454 nm, while exciting with 351 nm, and 530-555 nm, while exciting with 488 nm. The microscope, laser, spectrophotometer, image capture, and analysis all were under computer control.

The presence of the culture media did not add appreciable background to the autofluorescence images, as determined by comparison to imaging cells washed in PBS. This was presumably due to the low quantum yield of the medium at the excitation and emission wavelengths used, coupled with the inherent reduction in background from confocal sectioning. For image comparisons, experimental conditions including radiation exposure, scan rate, sample preparation, and sample temperature were held constant. Laser power directly at the sample could not be monitored, thus making quantitative comparisons difficult. Nonetheless, to minimize these limitations, and to make reasonable qualitative comparisons, images were acquired within the shortest time possible of each other, and no sample was used for more than 45 minutes.

What is claimed is:

1. An apparatus for measuring spectral and temporal fluorescence properties of tissue and cells in vivo comprising:
   (a) a primary excitation light source which is directed to a tissue or cell sample,
   (b) an optical fiber probe which delivers light to the tissue or cell sample and collects resulting fluorescent emissions from said tissue or cell sample wherein said primary excitation light source is directed through the optical fiber probe to the tissue or cell sample;
   (c) a means of directing the returning fluorescent emissions from the tissue or cell sample to spectral and temporal detection schemes;
   (d) a spectrometer coupled ICCD which detects fluorescent emissions output from the tissue or cell sample and derives therefrom spectral fluorescence properties of the tissue or cell sample;
   (e) an avalanche photodiode to detect temporal fluorescent emissions output from the tissue or cell sample; and
   (f) an oscilloscope for transiently digitizing a signal from the avalanche photodiode and deriving temporal fluorescence properties of the tissue or cell sample from the signal, said oscilloscope being connected to the avalanche photodiode.

* * * * *